(12) United States Patent
Dahl et al.

(10) Patent No.: US 6,342,185 B1
(45) Date of Patent: Jan. 29, 2002

(54) COMBINATORIAL CATALYTIC REACTOR

(75) Inventors: Ivar M. Dahl; Arne Karlsson; Duncan E. Akporiaye, all of Oslo (NO); Kurt M. Vanden Bussche, Lake-in-the-Hills; Gavin P. Towler, Barrington, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/464,171

(22) Filed: Dec. 15, 1999

(51) Int. Cl.$^7$ ............................................... G01N 31/10
(52) U.S. Cl. ...................... 422/82.12; 422/99; 422/101; 422/102; 422/104; 422/103; 422/130; 436/37
(58) Field of Search ................................ 422/82.12, 99, 422/101, 102, 103, 104, 130, 139; 436/34, 37, 155, 159, 161, 173

(56) References Cited

U.S. PATENT DOCUMENTS

| 3,431,077 A | * | 3/1969 | Danforth |
| 4,014,657 A | | 3/1977 | Gryaznov et al. ........ 23/288 R |
| 4,099,923 A | * | 7/1978 | Milberger |

(List continued on next page.)

FOREIGN PATENT DOCUMENTS

| JP | 62-87240 | * | 4/1987 | |
| WO | WO96/11878 A1 | | 4/1996 | ............ C01G/51/04 |
| WO | WO97/30784A-1 | | 8/1997 | ............ B01J/19/00 |
| WO | WO97/32208 A1 | | 9/1997 | ............ H01J/49/00 |
| WO | WO98/07026 A1 | | 2/1998 | ............ G01N/31/10 |
| WO | WO98/36826 A1 | | 8/1998 | ............... B01J/3/00 |
| WO | WO98/39099 | | 9/1998 | ............... B01L/3/00 |
| WO | WO99/19724 A1 | | 4/1999 | ........... G01N/31/10 |
| WO | WO99/34206 A1 | | 7/1999 | ........... G01N/33/10 |
| WO | WO 99/64160 | | 12/1999 | ............... B01L/3/02 |
| WO | WO 00/09255 | | 2/2000 | ............... B01J/19/00 |

OTHER PUBLICATIONS

Akporiaye, D. E.; Dahl, I. M.; Karlsson, A.; Wendelbo, R. *Angew Chem. Int. Ed.* 1998, 37, 609–611.

Holzwarth, A.; Schmidt, H.; Maier, W. F. *Angew. Chem. Int. Ed.*, 1998, 37, 2644–2647.

Bein, T. *Angew. Chem. Int. Ed.*, 1999, 38, 323–326.

Senkam, S. M. *Nature*. Jul. 1998, 384(23), 350–353.

Taylor, S. J.; Morken, J. P. *Science*, Apr. 1998, 280(10), 267–270.

Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 38, 484–488.

Klien, J.; Lehmann, C. W.; Schmidt. H.; Maier, W. F. *Angew Chem. Int.* Ed. 1998, 37, 3369–3372.

M. Dimitrov et al, God. Vissh. Khimikotekhnol. Inst., Sofia 1972, 19, 15–26.*

(List continued on next page.)

*Primary Examiner*—Arlen Soderquist
(74) *Attorney, Agent, or Firm*—John G. Tolomei; Frank S. Molinaro; Maryann Maas (57) ABSTRACT

A reactor for conducting catalytic chemical reactions has been developed. The reactor has a well having an open end and a closed end. The reactor also has a sleeve having a top end and a bottom end. The bottom end of the sleeve is inserted within the open end of the well. A fluid permeable structure is attached to the sleeve spanning the cross-section thereby defining a chamber between the closed end of the well and the fluid permeable structure. The reactor also has a reactor insert having a fluid permeable end and a top end containing a first and a second fluid conduit. The fluid permeable end of the reactor is inserted within the open end of the sleeve. The first fluid conduit is in fluid communication with the chamber, and the second fluid conduit is in fluid communication with the fluid permeable end of the reactor insert.

43 Claims, 4 Drawing Sheets

U.S. PATENT DOCUMENTS

| | | | | |
|---|---|---|---|---|
| 4,962,044 A | * | 10/1990 | Knesel, Jr. et al. | 436/177 |
| 5,112,574 A | | 5/1992 | Horton | 422/102 |
| 5,304,354 A | | 4/1994 | Finley et al. | 422/196 |
| 5,405,586 A | | 4/1995 | Koves | 422/218 |
| 5,425,921 A | * | 6/1995 | Coakley et al. | 422/102 |
| 5,489,726 A | | 2/1996 | Huss, Jr. et al. | 585/671 |
| 5,609,826 A | | 3/1997 | Cargill et al. | 422/99 |
| 5,612,002 A | | 3/1997 | Cody et al. | 422/131 |
| 5,746,982 A | | 5/1998 | Saneii et al. | 422/134 |
| 5,766,556 A | | 6/1998 | DeWitt et al. | 422/131 |
| 5,785,927 A | | 7/1998 | Scott et al. | 422/104 |
| 5,792,431 A | | 8/1998 | Moore et al. | 422/134 |
| 6,030,917 A | | 2/2000 | Weinberg et al. | 502/104 |
| 6,045,671 A | | 4/2000 | Wu et al. | 204/298.11 |
| 6,056,926 A | | 5/2000 | Sugarman et al. | 422/131 |
| 6,063,633 A | * | 5/2000 | Willson, III | 436/37 |

OTHER PUBLICATIONS

G. P. Korneichuk et al, Kinet. Katal. 1977, 18, 244–247.*

W. A. Smigiel et al, Ind. Eng. Chem. Fundam. 1979, 18, 419–422.*

P. C. M. van Woerkom et al, Appl. Opt. 1980, 19, 2546–2550.*

M. Steininger et al, J. Chromatog. 1982, 243, 279–284.*

J. G. Creer et al, Appl. Catal. 1986, 22, 85–95.*

U. Rodemerck et al, Microreact. Technol.: Ind. Prospects, Proc. Int. Conf., 3rd 1999, Springer–Verlag: Berlin, Germany, pp. 287–293.*

* cited by examiner

COMBINATORIAL CATALYTIC REACTOR

FIELD OF THE INVENTION

The invention relates to a reactor for evaluating catalysts, and particularly to a plurality of reactors for combinatorial chemistry.

BACKGROUND OF THE INVENTION

Developments in combinatorial chemistry have largely concentrated on the synthesis of chemical compounds. For example, U.S.Pat. Nos. 5612002 and 5766556 disclose a method and apparatus for multiple simultaneous synthesis of compounds.

WO 97/30784-A1 discloses a microreactor for the synthesis of chemical compounds. Akporiaye, D. E.; Dahl, I. M.; Karlsson, A.; Wendelbo, R. *Angew Chem. Int. Ed.* 1998, 37, 609–611 disclose a combinatorial approach to the hydrothermal synthesis of zeolites, see also WO 98/36826-A1. Other examples include U.S. Pat. Nos. 5609826, 5792431, 5746982, and 5785927, and WO 96/11878-A1.

More recently, combinatorial approaches have been applied to catalyst testing to try to expedite the testing process. For example, WO 97/32208-A1 teaches placing different catalysts in a multicell holder. The reaction occurring in each cell of the holder is measured to determine the activity of the catalysts by observing the heat liberated or absorbed by the respective formulation during the course of the reaction and/or analyzing the products or reactants. Thermal imaging had been used as part of other combinatorial approaches to catalyst testing, see Holzwarth, A.; Schmodt, H.; Maier, W. F. *Angew. Chem. Int. Ed.,* 1998, 37, 2644–2647, and Bein, T. *Angew. Chem. Int. Ed.,* 1999, 38, 323–326. Thermal imaging may be a tool to learn some semi-quantitative information regarding the activity of the catalyst, but it provides no indication as to the selectivity of the catalyst.

Some attempts to acquire information as to the reaction products in rapid-throughput catalyst testing are described in Senkam, S. M. *Nature,* Jul. 1998, 384(23), analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 38, 484–488 teaches using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

Combinatorial chemistry has been applied to evaluate the activity of catalysts. Some applications have focused on determining the relative activity of catalysts in a library; see Klien, J.; Lehmann, C. W.; Schmidt, H.; Maier, W. F. *Angew Chem. Int. Ed.* 1998, 37, 3369–3372; Taylor, S. J.; Morken, J. P. *Science,* Apr. 1998, 280(10), 267–270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons which are detected by microelectrode collection. WO 98/07026-A1 discloses miniaturized reactors where the reaction mixture is analyzed during the reaction time using spectroscopic analysis. Some commercial processes have operated using multiple parallel reactors where the products of all the reactors are combined into a single product stream; see U.S. Pat. Nos. 5304354 and 5489726.

Applicants have developed a reactor particularly suited for use in combinatorial evaluation of catalysts. Multiple reactors may be readily assembled in an array for the simultaneous evaluation of a number of catalysts. The wells of the multiple reactors may be integrated into a single block, and the reactor inserts of the multiple reactors may be integrated into a single top plate thereby allowing for easy handling and assembly of an array of multiple reactors.

SUMMARY OF THE INVENTION

The invention is a reactor for conducting catalytic chemical reactions. The reactor has a well having an open end and a closed end and a first seal retained by the open end of the well. The reactor also has a sleeve having an open end and a bottom end. The bottom end of the sleeve is inserted within the open end of the well. A fluid permeable structure is attached to the sleeve spanning the cross-section of the sleeve and thereby defining a chamber between the closed end of the well and the fluid permeable structure attached to the sleeve. The reactor also has a reactor insert having a fluid permeable end and a top end containing a first and a second fluid conduit. The fluid permeable end of the reactor is inserted within the open end of the sleeve. The top end of the reactor insert is engaged with the first seal. The first fluid conduit is in fluid communication with the chamber; and the second fluid conduit is in fluid communication with the fluid permeable end of the reactor insert. A second seal retained by the reactor insert is engaged with the sleeve.

A preferred embodiment of the invention is one where the apparatus is a plurality of individual reactors, each reactor as described above. Another preferred embodiment of the invention is one where a plurality of wells are attached to a single support, and the corresponding plurality of reactor inserts are attached to a single top plate.

DETAILED DESCRIPTION OF THE INVENTION

In general terms, the invention is a reactor for use in combinatorial applications and a process for conducting a combinatorial catalyzed reaction. In combinatorial applications, the reactor of the present invention is used as an array of multiple reactors operating simultaneously in parallel. Preferably the reactor consists of three main components, (I) a top, or reactor insert, (II) a sleeve, and (III) a bottom, or well. Each of the main components may be constructed out of materials suitable to the application contemplated. The materials chosen are selected to withstand the temperatures, pressures and chemical compounds of the particular application. Examples of suitable materials include metals and their alloys, low grade steel, and stainless steels, super-alloys like incollsy, inconel, hastalloy, engineering plastics and high temperature plastics, ceramics such as silicon carbide and silicon nitride, glass, and quartz. It is not necessary that each component be made of the same material.

The well is preferably cylindrical in shape, but may be of other geometric shapes. For example, the cross-section of the well may be in the shape of a square, an ellipse, a rectangle, a polygon, "D"-shaped, segment- or pie-shaped, a chard, or the like. For ease of discussion, the well is discussed here as having a cylindrical shape. The well has a top end, sides, and a bottom end. The top end is open and the bottom end is permanently closed. The preferred volume of the well ranges from about 0.001 cm$^3$ to about 10 cm$^3$ with two most preferred volumes being 0.1 cm$^3$ and 1 cm$^3$. The preferred size of the well ranges from a length/diameter ratio of about 1 to about 20. It is more preferred that the length/diameter of the wells be greater than 4 and ideally 5 or 10. It is preferred that the well be constructed of material that is able to withstand temperatures of from about 10° C. to about 1000° C. It is also preferred that the well be constructed of material having good heat transfer properties and that the material of construction is inert in the reaction being conducted in the reactor.

The well may be a freestanding unit, or multiple wells may be formed from a single tray or block of material. It is preferred to have a single tray, rack, or support to which multiple wells are attached. For example, a single unit such as a tray, rack, or block of material may support 6, 8, 12, 24, 48, 96, 382 or 1264 wells. It is most preferred that the single unit be similar to the dimensions of a commonly used microtiter tray. The multiplicity of wells may be heated as a unit, or each well may be individually heated. It is preferred that the heater be positioned adjacent the wells. It is preferred that the open end of the well be flanged. The flange of the open end of the well is used to retain a seal such as an o-ring. The seal engages the reactor insert (discussed in detail below) and operates to form a pressure-tight seal between the well and the reactor insert. Alternate pressure seals may be employed such as VCR, or hoefer fittings, but o-rings are preferred. Optionally, the well may contain a projection extending from the side of the well partially into the interior of the well to properly position and retain the sleeve (discussed below) within the well. The projection is located at the closed end of the well, at a location where the bottom end of the sleeve (discussed below) rests on the projection. The projection may be any of various possibilities of support such as a ledge, lip, or a shelf extending from the side of the well into the interior of the well. It is more preferred, however, that the sleeve be self-supporting within the well as discussed below.

In the preferred embodiment, a reactor insert is inserted into a sleeve which in turn is inserted into the well. In the assembled reactor, the sleeve is positioned between the reactor insert and the well. As with the well, the sleeve is preferably cylindrical in shape, but may be of other geometric shapes. For example, the general cross-section of the sleeve may be in the shape of a square, an ellipse, a rectangle, a polygon, "D"-shaped, segment- or pie-shaped, cog- or gear-shaped, a chard, or the like. It is preferred that the geometry of the sleeve is chosen to coordinate with the geometry of the well. It is most preferred that the sleeve is cylindrical, and for ease of discussion, the sleeve is discussed here as having an overall cylindrical shape.

The sleeve has a top end, sides, and a bottom end. The top and bottom ends of the sleeve are open. A microporous containment device, which may be constructed of any material that is capable of retaining solid particles while allowing gas or liquid to pass through, is attached at or near the bottom end of the sleeve and extends across the cross-section, or internal diameter, of the sleeve. Examples include frits, membranes, or fine meshed screens. Suitable frits include sintered metal, glass, sintered glass, and raney metals. Suitable membranes include electro-bonded films and etched alloy films. Frits are preferred for the microporous containment device at or near the bottom of the sleeve, and it is preferred that the frit cover as much of the cross-section of sleeve as possible, and most preferred that the frit cover as close to 100 percent of the cross-section of the sleeve as practical. It is most preferred to have a frit with small passages so that the fluid is well dispersed after passing through the frit. The interior volume of space defined by the top of the sleeve, sides of the sleeve, and the microporous containment device attached to the sleeve is a reaction zone and contains solid catalyst particles.

The external diameter of the sleeve is less than the internal diameter of the well so that the sleeve may be inserted into the well. In one embodiment of the invention, the length of the sleeve may be less than the length of the well so that a chamber is formed between the bottom end of the sleeve and the bottom end of the well. It is preferred that the length of the sleeve be from about 70% to about 95% of the length of the well. In another more preferred embodiment of the invention, the sleeve extends the entire length of the well with the bottom end of the sleeve resting on the bottom of the well. In this embodiment, the microporous containment device is located near but not at the bottom end of the sleeve. Furthermore, in this embodiment, the sides of the sleeve at the bottom end of the sleeve have portions removed so that as the bottom end of the sleeve rests on the bottom end of well, channels are formed through which fluid is able to flow. For example, the bottom end of the sleeve may have ridges, or may be scalloped or grooved.

It is preferred that the sleeve is constructed of material that is able to withstand temperatures of from about 10° C. to about 1000° C. and it is preferred that the sleeve be constructed of material as was used for the well. It is also preferred that the sleeve be constructed of material having good heat transfer properties.

The sleeve and the well are sized so that with the sleeve inserted into the well, the external surface of the sleeve and the internal surface of the well form channels through which a fluid is able to flow. It is preferred that either the external surface of the sleeve or the internal surface of the well, or both, define grooves that upon insertion of the sleeve into the well form the channels. The grooves may run parallel to the length of the sleeve, may follow the circumference of the sleeve in a spiral pattern, or may form a wave pattern. The channels formed by the grooves provide a path for fluid to flow from one end of the sleeve to the other. For example, the fluid may flow from the top of the sleeve to the chamber formed between the fluid permeable structure attached to the sleeve and the bottom of the well. From the chamber between the fluid permeable structure attached to the sleeve and the bottom of the well, the fluid may pass through the permeable structure attached to the sleeve and into the reaction zone containing the solid catalyst particles.

The sleeve is preferably sized, and the grooves formed, so that a portion of the external surface of the sleeve remains in contact with the internal surface of the well. Such contact provides for good heat transfer from the well to the sleeve. Many reactions require heat, and good heat transfer from the well to the sleeve provides a mode for heating the reaction zone defined by the sleeve and the catalyst within the reaction zone. It is generally desirable to preheat the reactant prior to introduction to the reaction zone, and good heat transfer between the well and the sleeve provides for an opportunity to preheat the reactant as it passes with the fluid flow through the channels. The pattern chosen for the grooves may vary depending upon the degree of preheating needed for the reactant and the particular reaction involved. For example, grooves and therefore channels that run parallel to the length of the sleeve would provide less residence time of the fluid within the channels and less preheating. On the other hand, grooves and channels that spiral around the circumference of the sleeve provide greater residence time of the fluid within the channels and greater preheating, but may allow time for background reactions to occur.

A reactor insert is inserted into the sleeve. The reactor insert also has a top end, sides, and a bottom end containing a fluid permeable portion. As with the well and the sleeve, the reactor insert is preferably cylindrical in shape, but may be of other geometric shapes such as a cross-section in the shape of a square, an ellipse, a rectangle, a polygon, "D"-shaped, segment- or pie-shaped, cog- or gear-shaped, a chard, or the like. However, with the reactor insert, it is preferable to have the geometry of the reactor insert conform to the geometry of the interior of the sleeve. For ease of discussion, the reactor insert is discussed here as having a cylindrical shape. The top end provides a fluid conduit and the bottom end contains a fluid permeable portion. It is preferred that the reactor insert be constructed of material that is able to withstand temperatures of from about 10° C. to about 1000° C. and it is preferred to construct the reactor insert from the same material as the well and the sleeve.

The external diameter of the reactor insert is less than the internal diameter of the sleeve so that the reactor insert may be inserted into the sleeve. The length of the reactor insert is less than the length of the sleeve measured from the top of the sleeve to the fluid permeable structure attached to the sleeve, so that a reaction zone is formed between the bottom end of the reactor insert and the fluid permeable structure attached to the sleeve. Solid catalyst particles are retained within the reaction zone. It is preferred that the length of the reactor insert be from about 5% to about 70% of the length of the sleeve measured from the top of the sleeve to the fluid permeable structure attached to the sleeve.

As stated above, the bottom end of the reactor insert contains at least a portion that is permeable to fluid. The portion permeable to fluid may be any material that is capable of excluding solid particles while allowing gas or liquid to pass through. Examples include frits or membranes as discussed above for the sleeve. Frits are preferred for the permeable portion of the bottom of the reactor insert, and it is preferred that the frit cover from about 20 to greater than 90 percent of the bottom of the reactor insert with the most preferred being greater than 90 percent of the bottom of the reactor insert. The interior of the reactor insert forms a passage to allow fluid to flow from one end of the reactor insert to the other. For example, the fluid that permeates through the permeable portion of the bottom end of the reactor insert may pass to the top end of the reactor insert and exit the reactor via the fluid conduit at the top end of the reactor insert. Catalyst particles are unable to pass through the permeable portion of the bottom end of the reactor insert and are therefore retained within the reaction zone.

It is preferred that the top end of the reactor insert be flanged. The flanged portion of the reactor insert would engage the o-ring seal retained by the flange of the well to form a pressure-tight seal between the reactor insert and the well via the o-ring. The reactor insert is further equipped with a seal to engage the sleeve and form a pressure-tight seal between the reactor insert and the sleeve. Optionally, the reactor insert may be equipped with a thermocouple. The thermocouple may extend from the top of the reactor insert, through the interior passage of the reactor insert, and through the bottom of the reactor insert to extend into the reaction zone. The thermocouple provides accurate measurements of the temperature at which a reaction in the reaction zone is occurring. It is preferred that the thermocouple be housed within a guide tube that also extends from the top of the reactor insert, through the interior passage of the reactor insert, and through the bottom of the reactor insert into the reaction zone. The guide tube, which is open at both a top end and a bottom end, allows for easy insertion or removal of the thermocouple.

As discussed above, one fluid conduit is located at the top end of the reactor insert. A second fluid conduit may be positioned in a variety of locations to allow fluid to pass to or exit from the channels formed by the sleeve and the well. A preferred location for the second fluid conduit is for the conduit to pass through the flange of the reactor insert and conduct fluid into a volume of space between the flange of the reactor insert and the flange of the well. The volume of space is further defined by the o-ring seal retained by the flange of the well and the side of the reactor insert. Alternatively, the second fluid conduit may pass through the side of the well and provide a passage for fluid to flow into or out of the channels formed by the sleeve and the well. It is preferred that the second fluid conduit pass through the flange of the reactor insert to the volume of space between the flange of the reactor insert and the flange of the well so that all fluid conduits are a part of the reactor insert. In a specific embodiment of the invention either the first or the second fluid conduit is in fluid communication with a reactant reservoir. Similarly, the fluid conduit that is not in fluid communication with a reactant reservoir may be in fluid communication with a sampling device that is used to sample the effluent exiting the reactor.

In combinatorial applications, an array of reactors are used in parallel to conduct multiple reactions simultaneously. The preferred reactor described above is successfully used in combinatorial applications. It is preferred that the multiple wells of a number of reactors are attached to a single support such as a rack or tray (described above). The multiple reactor inserts are also preferably attached to a single support such as a top plate. For combinatorial applications, a single top plate is engaged with a single rack containing multiple wells to form a multiple of individual reactors. It is preferred to have the sleeves be individually movable however. The reactor sleeves may be used in the synthesis of different catalysts, and the sleeves, still containing the catalysts, are inserted into the wells as described above. The advantage would be the elimination of a catalyst transfer step since the catalyst would remain in the sleeve from the time of synthesis through the testing process. It is preferred to have the same reactant reservoir in fluid communication with each of the multiple reactors.

Figures 1, 2, 3:
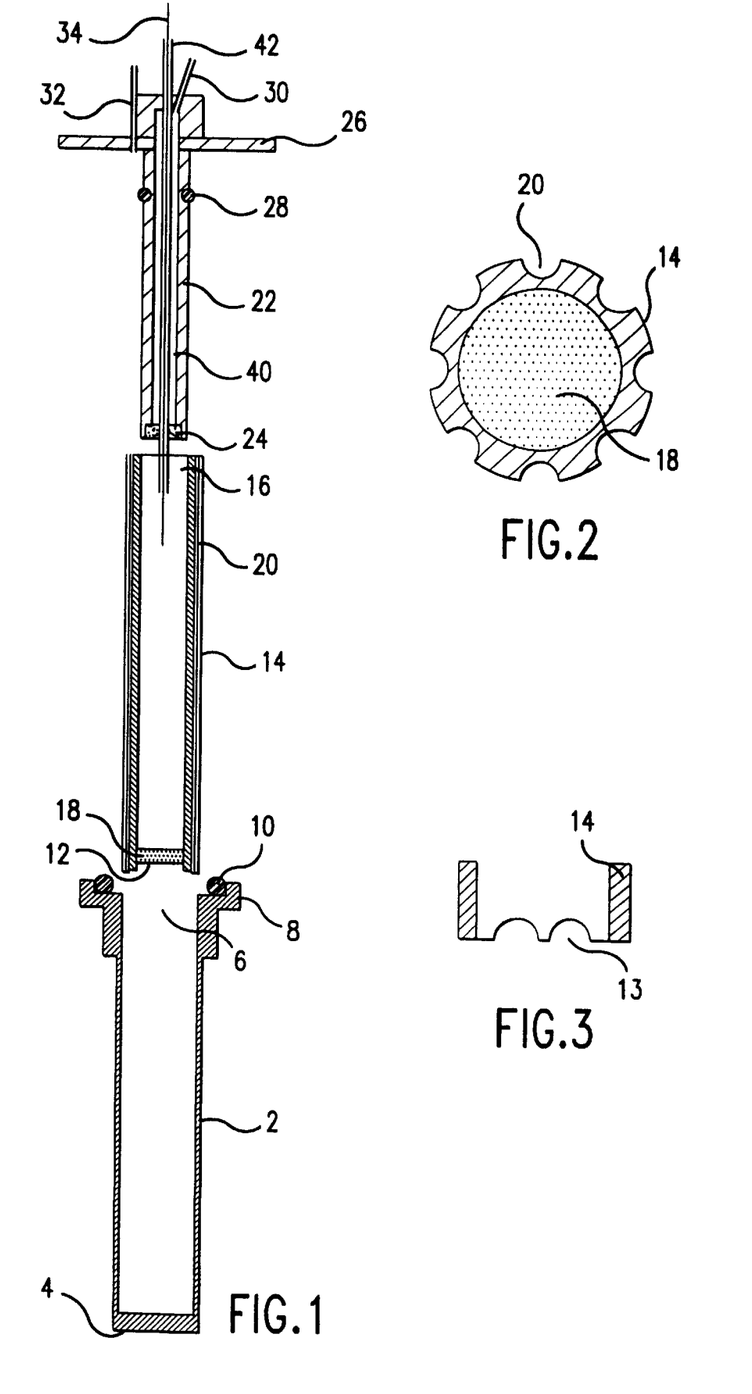
FIG. 1 is an exploded side view of a preferred reactor.
FIG. 2 is an end view of the sleeve of the preferred reactor.
FIG. 3 is an enlarged view of the bottom end of the sleeve of the preferred reactor.
Figure 4:
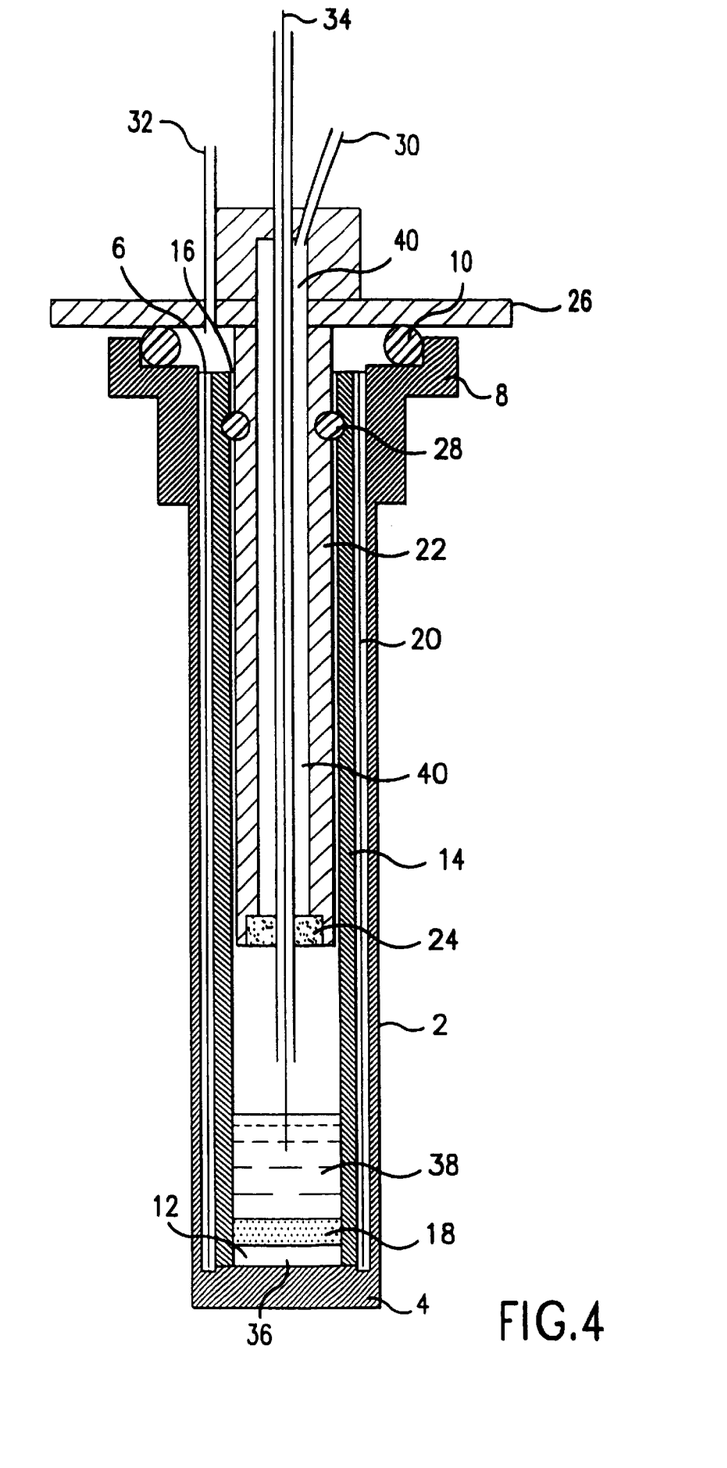
FIG. 4 is an assembled side view of the preferred reactor.

Referring to FIG. 1, an exploded side view of the reactor of the invention, well 2, has a closed end 4 and an open end 6. Open end 6 contains a flange 8 which retains o-ring 10. Sleeve 14 has open end 16 and bottom end 12. Near the bottom end 12 is frit 18. The walls of sleeve 14 have material removed to form grooves 20 as shown in FIG. 2, an end view of sleeve 14. The bottom end 12 of sleeve 14 has material removed to form ridges 13, as shown in FIG. 3, and external side view of bottom end 12 of sleeve 14. Reactor insert 22 has fluid permeable end 24 in fluid communication with fluid conduit 30 via hollow center 40. Reactor insert 22 has flanged end 26, fluid conduit 32, and o-ring 28. Thermocouple 34 extends through guide tube 42 which in turn extends through reactor insert 22 and beyond fluid permeable end 24 of reactor insert 22. Referring to FIG. 4, bottom end 12 of sleeve 14 is inserted into open end 6 of well 2 with bottom end 12 of sleeve 14 resting on closed end 4 of well 2. Fluid permeable end 24 of reactor insert 22 is inserted into open end 16 of sleeve 14. A reaction zone 38 is formed between the fluid permeable end 24 of reactor insert 22 and the frit 18 of sleeve 14. Catalyst is retained in reaction zone 38. Chamber 36 is formed by closed end 4 of well 2 and frit 18 of sleeve 14. Flange end 26 of reactor insert 22 engages o-ring 10 retained by flange 8 of well 2 to form a pressure tight seal. O-ring 28 of reactor insert 22 engages sleeve 14 to form a pressure tight seal.

Fluid enters the reactor via conduit 32. Grooves 20 of sleeve 14 together with well 2 form passages allowing fluid from conduit 32 to flow through grooves 20 and grooves 13 to chamber 36 formed by closed end 4 of well 2 and frit 18 of sleeve 14. Fluid passes through fluid permeable frit 18 of sleeve 14 and enters reaction zone 38 to contact the catalyst. The fluid flow may be at a rate to result in a fluidized bed of catalyst or fixed bed of catalyst, whichever is required for the specific application. Thermocouple 34 is used to accurately measure the temperature of reaction zone 38. After contacting the catalyst in reaction zone 38, the fluid passes through fluid permeable end 24 of reactor insert 22, through hollow center 40, and is removed from the reactor via fluid conduit 30.

Alternatively, fluid may be introduced to the reactor via fluid conduit 30. The fluid passes through hollow center 40 of reactor insert 22 and through fluid permeable end 24 of reactor insert 22 into reaction zone 38. With the fluid flowing in this direction, it is preferred that the flow rate be such that the catalyst remains as a fixed bed. After contacting the catalyst in reaction zone 38, the fluid passes through frit 18 of sleeve 14 and into chamber 36. The fluid then flows through passages formed by grooves 20 and 13 of sleeve 14 together with well 2 to the open flanged end 6 of well 2. The fluid exits the reactor via fluid conduit 32.

Figure 5:
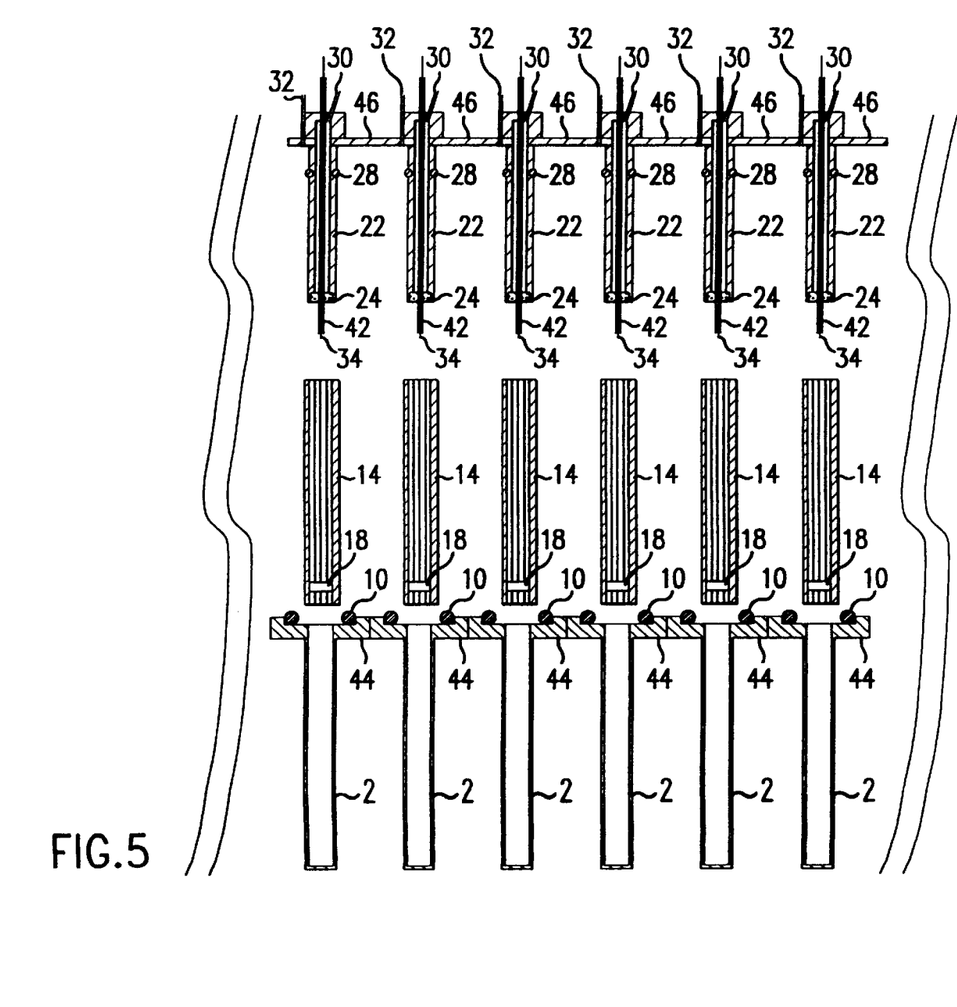
FIG. 5 is an exploded side view of a plurality of preferred reactors.

Turning now to FIG. 5 which is an exploded side view of an array of reactors having wells 2 sleeves 14 and reactor inserts 22. The wells 2 are as described above including retaining o-rings 10. However, the multiple wells 2 are attached to a support 44. The sleeves 14 are as described above, including the attachment of frits 18. Reactor inserts 22 are as described above including having fluid permeable ends 24 in fluid communication with fluid conduits 30, thermocouples 34 extending through guide tubes 42, fluid conduits 32, and o-rings 28. Reactor inserts 22 are attached to a top plate 46.

Figure 6:
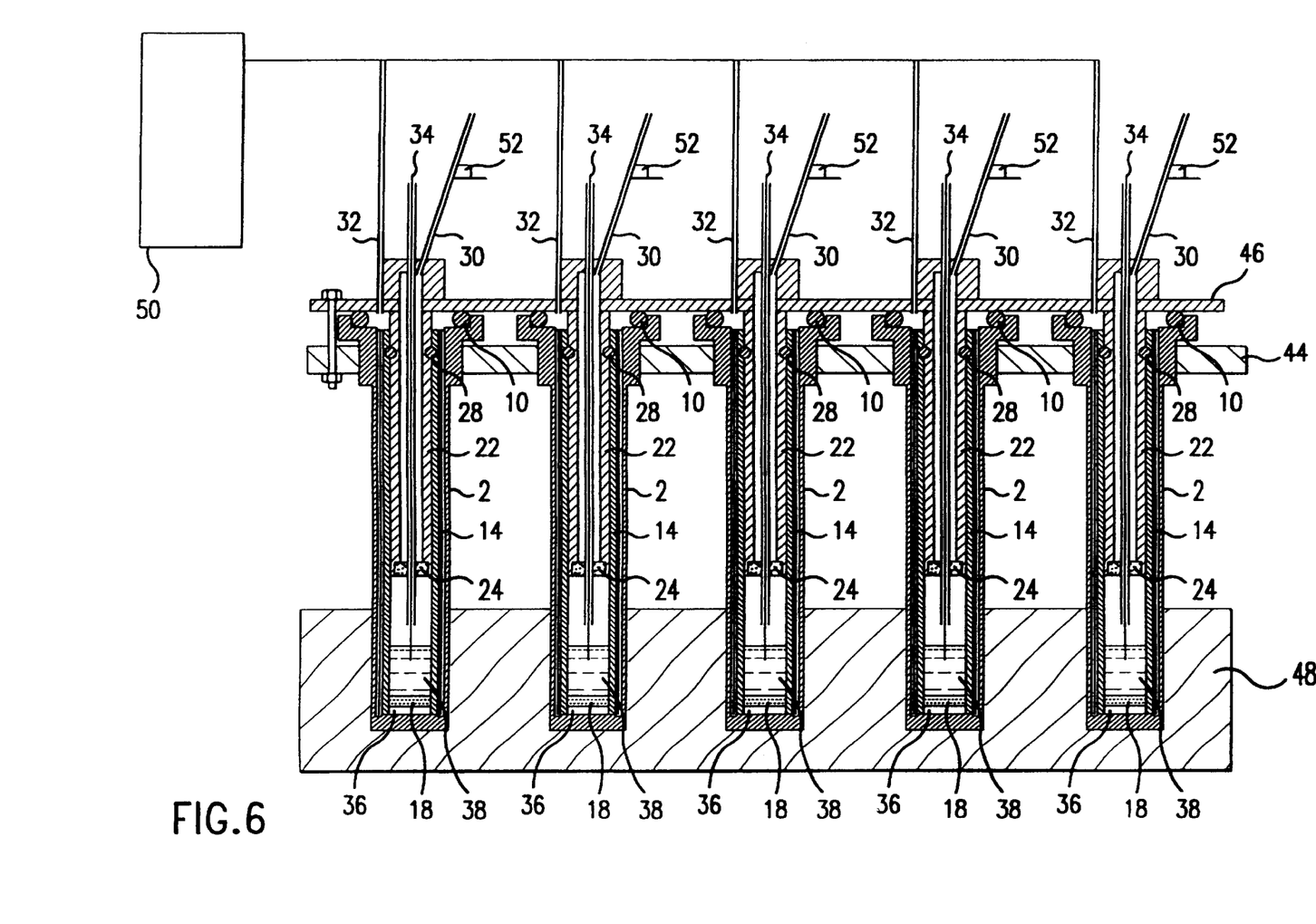
FIG. 6 is an assembled side view of a plurality of preferred reactors.

Referring to FIG. 6, sleeves 14 are inserted into wells 2. Fluid permeable ends 24 of reactor inserts 22 are inserted into sleeves 14. Reaction zones 38 are formed between the fluid permeable ends 24 of reactor inserts 22 and the frits 18 of sleeves 14. Catalyst is retained in reaction zones 38. Chambers 36 are formed by wells 2 and frits 18 of sleeves 14. Reactor inserts 22 engage o-rings 10 retained by wells 2 to form a pressure tight seal. O-rings 28 of reactor inserts 22 engage sleeves 14 to form a pressure tight seal. Heater 48 is positioned adjacent wells 2 and reaction zones 38. Fluid conduits 32 are connected to solvent reservoir 50, and fluid conduits 30 are equipped with sampling devices 52. In an alternate embodiment, Fluid conduits 30 may be connected to a solvent reservoir, and fluid conduits 32 be equipped with sampling devices.

What is claimed is:
1. An apparatus for conducting a catalyst evaluation comprising:
   a) a well having an open end and a closed end;
   b) a first seal retained by said open end of said well;
   c) a sleeve having a top end, a bottom end, and a cross-section, said bottom end inserted within said open end of the well;
   d) a fluid permeable structure attached to said sleeve at least partially spanning the cross-section of said sleeve and defining a chamber between said closed end of the well and said fluid permeable structure;
   e) a reactor insert having a fluid permeable end and a top end containing a first and a second fluid conduit, said fluid permeable end inserted within said open end of said sleeve to define a reaction zone, said top end of the reactor insert engaged with said first seal, said first fluid conduit in fluid communication with said chamber; and said second fluid conduit in fluid communication with said fluid permeable end of said reactor insert; and
   f) a second seal retained by said reactor insert and engaged with said sleeve.

2. The apparatus of claim 1 wherein the open end of the well is flanged.

3. The apparatus of claim 1 wherein the top end of the reactor insert is flanged.

4. The apparatus of claim 1 wherein said well is cylindrical.

5. The apparatus of claim 1 wherein said sleeve is cylindrical.

6. The apparatus of claim 1 wherein said reactor insert is cylindrical.

7. The apparatus of claim 1 wherein the bottom end of said sleeve has material removed to form grooves.

8. The apparatus of claim 1 further comprising said sleeve having a length, an internal surface, and an external surface where material is removed to form grooves in the external surface of the sleeve.

9. The apparatus of claim 8 wherein said grooves extend in a pattern selected from the group consisting of:
   a) a straight pattern along said length from said top end of said sleeve to said bottom end of said sleeve;
   b) a wave pattern along said length from said top end of said sleeve to said bottom end of said sleeve; and
   c) a spiral pattern around the circumference of said sleeve from said top end of said sleeve to said bottom end of said sleeve.

10. The apparatus of claim 1 further comprising said well having a length, an internal surface, and an external surface where material is removed to form grooves in the internal surface of said well.

11. The apparatus of claim 10 wherein said grooves extend in a pattern selected from the group consisting of:
   a) a straight pattern along said length from said open end to said closed end of said well;
   b) a wave pattern along said length from said open end to said closed end of said well; and
   c) a spiral pattern in the internal surface of the well extending from said open end to said closed end of said well.

12. The apparatus of claim 1 wherein said first and second seals are o-rings.

13. The apparatus of claim 1 further comprising a thermocouple retained by the reactor insert and extending into said reaction zone.

14. The apparatus of claim 1 further comprising a guide tube retained by the reactor insert and extending into said reaction zone, and a thermocouple retained by said guide tube.

15. The apparatus of claim 1 further comprising a projection within said well to engage said bottom end of said sleeve.

16. The apparatus of claim 1 further comprising a reactant reservoir in fluid communication with said first fluid conduit.

17. The apparatus of claim 1 further comprising a reactant reservoir in fluid communication with said second fluid conduit.

18. The apparatus of claim 1 further comprising a sampling device in fluid communication with said first conduit.

19. The apparatus of claim 1 further comprising a sampling device in fluid communication with said second conduit.

20. An apparatus for conducting multiple simultaneous catalyst evaluations comprising:
   a) a plurality of wells each having an open end and a closed end;
   b) a plurality of first seals each retained by an open end of said wells;
   c) a plurality of sleeves each having a top end, a bottom end, and a cross-section, said bottom ends inserted within said open ends of the wells;
   d) a plurality of fluid permeable structures attached to said sleeves at least partially spanning the cross-sections of the sleeves, defining a plurality of chambers between said closed end of said wells and said fluid permeable structures attached to said sleeves;
   e) a plurality of reactor inserts each having a top end containing a first and a second fluid conduit and a fluid permeable end, said fluid permeable ends of said reactor insert inserted within the top ends of the sleeves to define a plurality of reaction zones between the fluid permeable ends of the reactor inserts and the fluid permeable structures attached to the sleeves, said top ends of the reactor inserts engaged with the plurality of first seals, said first fluid conduits in fluid communication with said chambers, said second fluid conduits in fluid communication with said fluid permeable ends of the reactor inserts; and
   f) a plurality of second seals retained by the reactor inserts and engaged with the sleeves.

21. The apparatus of claim 20 wherein said open ends of said wells are flanged.

22. The apparatus of claim 20 wherein said top ends of said reactor inserts are flanged.

23. The apparatus of claim 20 wherein said plurality of wells are formed from a single unit of material.

24. The apparatus of claim 20 further comprising a support unit to which each of said wells is attached.

25. The apparatus of claim 20 wherein said plurality of reactor inserts are formed from a single unit of material.

26. The apparatus of claim 20 further comprising a top plate to which each of said reactor inserts is attached.

27. The apparatus of claim 20 wherein said wells are cylindrical.

28. The apparatus of claim 20 wherein said sleeves are cylindrical.

29. The apparatus of claim 20 wherein said reactor inserts are cylindrical.

30. The apparatus of claim 20 further comprising each of said sleeves having a length, an internal surface, and an external surface where material is removed to form grooves in the external surface of each of said sleeves.

31. The apparatus of claim 30 wherein said grooves extend in a pattern selected from the group consisting of:
   a) a straight pattern along said length from said top end of said sleeve to said bottom end of said sleeve;
   b) a wave pattern along said length from said top end of said sleeve to said bottom end of said sleeve; and
   c) a spiral pattern around the circumference of said sleeve from said top end of said sleeve to said bottom end of said sleeve.

32. The apparatus of claim 20 further comprising each of said wells having a length, an internal surface and an external surface where material is removed to form grooves in the internal surface of each of said wells.

33. The apparatus of claim 32 wherein said grooves extend in a pattern selected from the group consisting of:
   a) a straight pattern along said length from said open end to said closed end of said well;
   b) a wave pattern along said length from said open end to said closed end of said well; and
   c) a spiral pattern in the internal surface of the well extending from said open end to said closed end of said well.

34. The apparatus of claim 20 wherein material is removed from said bottom end of said sleeves to form grooves.

35. The apparatus of claim 20 wherein said plurality of first and second seals are o-rings.

36. The apparatus of claim 20 further comprising a plurality of thermocouples, at least one thermocouple retained by each said reactor insert.

37. The apparatus of claim 20 further comprising a plurality of guide tubes retained by the reactor inserts, said guide tubes housing a plurality of thermocouples.

38. The apparatus of claim 20 further comprising a plurality of projections, at least one projection within each said well to engage each said bottom end of said sleeve.

39. The apparatus of claim 20 further comprising a reactant reservoir in fluid communication with each said first fluid conduit.

40. The apparatus of claim 20 further comprising a reactant reservoir in fluid communication with each said second fluid conduit.

41. The apparatus of claim 20 further comprising a sampling device in fluid communication with each said first fluid conduit.

42. The apparatus of claim 20 further comprising a sampling device in fluid communication with each said second fluid conduit.

43. An apparatus for conducting multiple simultaneous catalyst evaluations comprising:
   a) a plurality of wells each having an open end and a closed end, each said well attached to a support;
   b) a heater adjacent to said wells;
   c) a plurality of first seals each retained by an open end of said wells;
   d) a plurality of sleeves each having a top end, a bottom end, and a cross-section, said bottom ends each inserted within said open ends of said wells;
   e) a plurality of fluid permeable structures attached to said sleeves and at least partially spanning the cross-section of said sleeves thereby defining a plurality of chambers between said closed end of said wells and said fluid permeable structures attached to said sleeves;
   f) a top plate attached to a plurality of reactor inserts each having a top end containing a first and a second fluid conduit and a fluid permeable end, said fluid permeable ends of said reactor inserts inserted within said open ends of said sleeves to define a plurality of reaction zones, said top ends of said reactor inserts engaged with said first seals, said first fluid conduits in fluid communication with said chambers; and said second fluid conduits in fluid communication with said fluid permeable ends of said reactor inserts;

g) a plurality of second seals retained by the reactor inserts and engaged with the sleeves; and h) a plurality of guide tubes attached to said reactor inserts and extending into said reaction zones, the plurality of guide tubes housing a plurality of thermocouples.

* * * * *